United States Patent [19]

Ogawa et al.

[11] Patent Number: 5,208,219

[45] Date of Patent: May 4, 1993

[54] METHOD FOR INDUCING BONE GROWTH

[75] Inventors: Yasushi Ogawa, Pacifica; David K. Schmidt, Santa Cruz; Rosa Armstrong, Palo Alto; Ranga Nathan, Newark; Andrea Y. Thompson, Mountain View; Saeid M. Seyedin, Saratoga, all of Calif.

[73] Assignee: Celtrix Pharmaceuticals Inc., Santa Clara, Calif.

[21] Appl. No.: 655,313

[22] Filed: Feb. 14, 1991

[51] Int. Cl.⁵ ............... A61K 37/02; A61K 37/36
[52] U.S. Cl. ............................. 514/12; 514/2; 514/8; 514/21; 530/399; 530/397; 530/350; 530/416; 530/417
[58] Field of Search .............. 514/2, 12, 8, 21; 530/417, 416, 399, 397, 350

[56] References Cited

U.S. PATENT DOCUMENTS 5,071,834 12/1991 Burton .................. 514/12

OTHER PUBLICATIONS

Vale et al., *Nature* (1986) 321:776–779.
Sawchemko et al., *Nature* (1988) 334:615–617.
Vale et al., *Recent progress in Hormone Research* (1988) 44:1–34.
Totsuka et al., *Biochem. Biophys. Res. Commun.* (1988) 156: 335–339.
Yu et al., *Nature* (1987) 330:765–767.
Broxmeyer et al., *Proc. Natl. Acad. Sci.* (1988) 85:9052–9056.
Murata et al., *Proc. Natl. Acad. Sci.* (1988) 85:2434–2438.
Cheifetz et al., *J. Biol. Chem.* (1988) 263(33):17225–17228.
Joyce et al., *J. Cell Biol.* (1990) 110:2195–2207.
Bentz et al., *J. Biol. Chem.* (1989) 264:20805–20810.
Meunier et al., *Proc. Natl. Acad. Sci.* (1988) 85:247–251.
Broxmeyer et al., *Exp Hematology*, (N.Y.), 16(6), 474, 1988, (Biosis abstract available).
Seyedin et al., *The J. of Biol. Chem.*, 261(13), 5693–5695, 1986.

*Primary Examiner*—F. T. Moezie
*Attorney, Agent, or Firm*—Morrison & Foerster

[57] ABSTRACT

Activin is administered systemically and locally to induce the growth of mature bone. Activin enhances the level of bone formation and the quality of the bone formed when administered locally with BMP or bone marrow. Administration of activin by subcutaneous route promotes systemic increase in the bone mass.

31 Claims, 4 Drawing Sheets

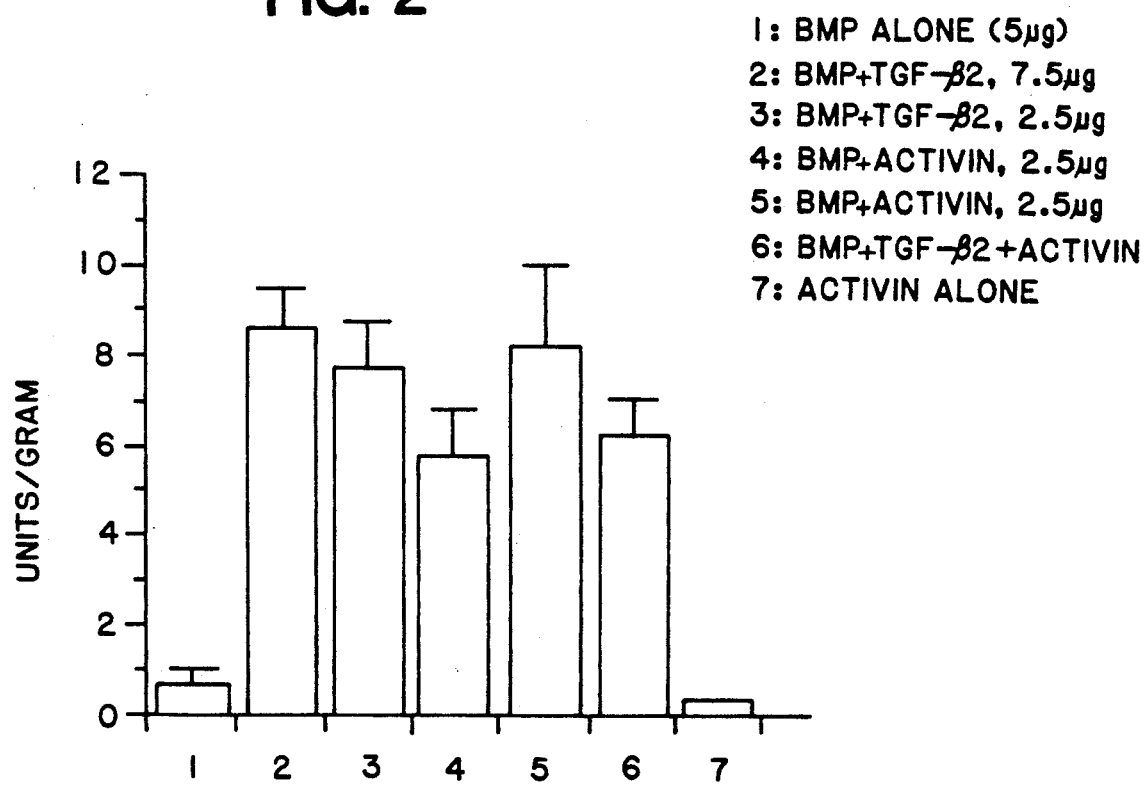

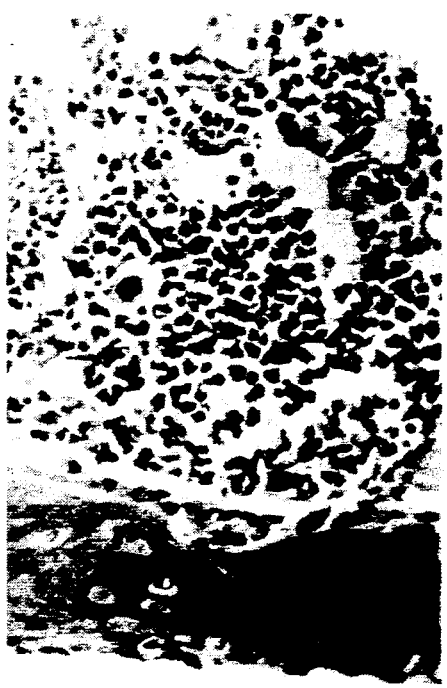
FIG. 3A vehicle alone
FIG. 3B 1μg TGF-β1/day
FIG. 3C 1μg activin/day GROUP 1: CERAMIC/COLLAGEN CARRIER ALONE
2: CERAMIC/COLLAGEN CARRIER+20 µl BONE MARROW
3: CERAMIC /COLLAGEN CARRIER+20 µl BONE MARROW
+ 5 µg ACTIVIN

METHOD FOR INDUCING BONE GROWTH

FIELD OF THE INVENTION

The invention relates to polypeptide factors and their use in bone growth and maturation. Specifically, the invention relates to the isolation and purification of activin from bone and its use in bone growth and maturation. The invention also relates to methods of (1) locally inducing mature bone growth and maturation by administering an osteogenically effective amount of activin in combination with bone morphogenic proteins (BMPs) and/or bone marrow; and (2) systemically inducing bone growth and maturation by administering an osteogenically effective amount of activin alone, or in combination with BMPs and/or bone marrow.

BACKGROUND OF THE INVENTION

Activins are dimeric proteins structurally similar to inhibin, TGF-$\beta$1, TGF-$\beta$2, and other proteins that makeup a family of proteins structurally related to TGF-$\beta$1. These proteins exhibit the chromatographic properties of TGF-$\beta$s. In addition to having homology with respect to the amino acid sequences, activins exhibit conservation of cysteine positions characteristic of the TGF-$\beta$s. Activins exhibit a molecular weight of 25 kD under nonreducing conditions by SDS-PAGE (and a molecular weight of 14 kD under reducing conditions). There are two known forms of the activin subunits, which have been termed $\beta$A or $\beta$B. Homodimeric forms $\beta$AA and $\beta$BB and a heterodimeric form $\beta$AB have been described in the literature. Activin subunits have about a 30% homology to TGF-$\beta$1 and TGF-$\beta$2 chains in terms of their amino acid sequences. Inhibins are polypeptides which are also structurally related to activins. Inhibins are heterodimers of the activin $\beta$A or $\beta$B subunit and a separate $\alpha$ subunit. Inhibins exhibit activity essentially opposite to activin.

The activin $\beta$A homodimer and $\beta$AB heterodimer have been purified from porcine ovarian follicular fluid, and have been shown to stimulate the release of follicle stimulating hormone (FSH) from rat pituitary cells in vitro (W. Vale et al., *Nature* (1986) 321:776-79). Other reported activities include stimulation of oxytocin release from neurosecretory neurons (P. E. Sawchemko, et al., *Nature* (1988) 334:615-17; W. Vale et al., "Recent progress in Hormone Research" (1988) 44:1-34); stimulation of insulin secretion from pancreatic islets (Y. Totsuka et al., *Biochem. & Biophys. Res. Comm.* (1988) 156:335-39); and stimulation of erythroid and multipotential progenitor cell colony formation in bone marrow culture (J. Yu et al., *Nature* (1987) 330:765-67; H. E. Broxmeyer et al., *Proc. Natl. Acad. Sci. U.S.A.* (1988) 85:9052-56). Activin $\beta$A is apparently identical to erythroid differentiation factor (EDF) (M. Murata et al., *Proc. Natl. Acad. Sci. U.S.A.* (1988) 85:2434-38).

Despite the fact that activin is similar in amino acid sequence to TGF-$\beta$, activin does not compete with TGF-$\beta$ for binding to TGF-$\beta$ receptors types I, II, or III present on fibroblasts and epithelial cells. However, activin has been reported to compete against binding of TGF-$\beta$1 to rat pituitary tumor cells (S. Cheifetz et al., *J. Biol. Chem.* (1988) 263:17225-28). TGF-$\beta$1 and TGF-$\beta$2 have been reported to induce formation of endochondral bone in vivo (M. E. Joyce et al., *J. Cell Biol.* (1990) 110:2195-2207, H. Bentz, et al. (1989) *J. Biol. Chem.*, 264:20805-10).

Although the mRNA encoding activin $\beta$A has been detected in several different tissues, including placenta, pituitary, bone marrow, kidney, spinal cord and brain (H. Meunier et al., *Proc. Natl. Acad. Sci U.S.A.* (1988) 85:247-51), to date the protein has been isolated only from porcine ovarian follicular fluid. What has not been reported is the isolation and purification of activin from bone and its ability to induce bone growth and maturation. Thus, there remains a need for the development of methodologies to extract activin from bone and to develop compositions and treatment modalities to induce bone growth and maturation. The present invention offers such.

SUMMARY OF THE INVENTION

Bone growth and maturation are enhanced by administering activin in a formulation and in an amount sufficient for inducing bone tissue deposition. Preferably, local bone growth and maturation is induced by administering osteogenically effective amounts of a combination of activin and TGF-$\beta$, BMPs and/or bone marrow or proteins extracted therefrom. Systemic bone growth and maturation preferably is induced by administering osteogenically effective amounts of activin alone, or in combination with TGF-$\beta$, BMPs and/or bone marrow or proteins extracted therefrom. The method of the invention results in the production of bone, with little or no cartilage.

The present invention further includes compositions for locally inducing the deposition of bone tissue comprising activin with TGF-$\beta$, BMPs, and/or bone marrow or proteins extracted therefrom.

Compositions for systemically inducing the deposition of bone tissue comprise activin alone, or in combination with TGF-$\beta$, BMPs and/or bone marrow or proteins extracted therefrom.

The compositions include pharmaceutical formulations, which can be administered locally and systemically, to induce bone growth and maturation, thereby effectively administered to treat bone disorders such as osteoporosis, osteohalisteresis, and osteomalacia.

Another object of the invention is to provide a method for locally inducing bone growth by administering activin alone or in combination with TGF-$\beta$, BMP, or bone marrow or proteins extracted therefrom, alone or in combination, in a dental or orthopedic implant.

Another object is to provide a method for extracting activin from bone and using the activin in a local or systemic treatment method to induce bone growth and maturation.

Another object of the invention is to provide a method for isolating and purifying activin $\beta$AA homodimer from bone tissue.

Another feature of the invention is to regulate bone growth and maturation by first administering an effective amount of TGF-$\beta$ and BMPs to induce bone formation, and secondly administering an effective amount of activin to induce bone maturation.

These and other objects, advantages and features of the present invention will become apparent to those persons skilled in the art upon reading the details of the isolation, purification, formulation and use as more fully set forth below, reference being made to the accompanying drawings forming a part hereof.

BRIEF DESCRIPTION OF THE DRAWINGS

FIG. 2 is a graph of the results obtained in an alkaline phosphatase assay at 14 days, as described in Example 3.

FIG. 3 is a histological graph of the results described in Example 4.

DETAILED DESCRIPTION OF THE INVENTION

A. Overview

Figure 1:
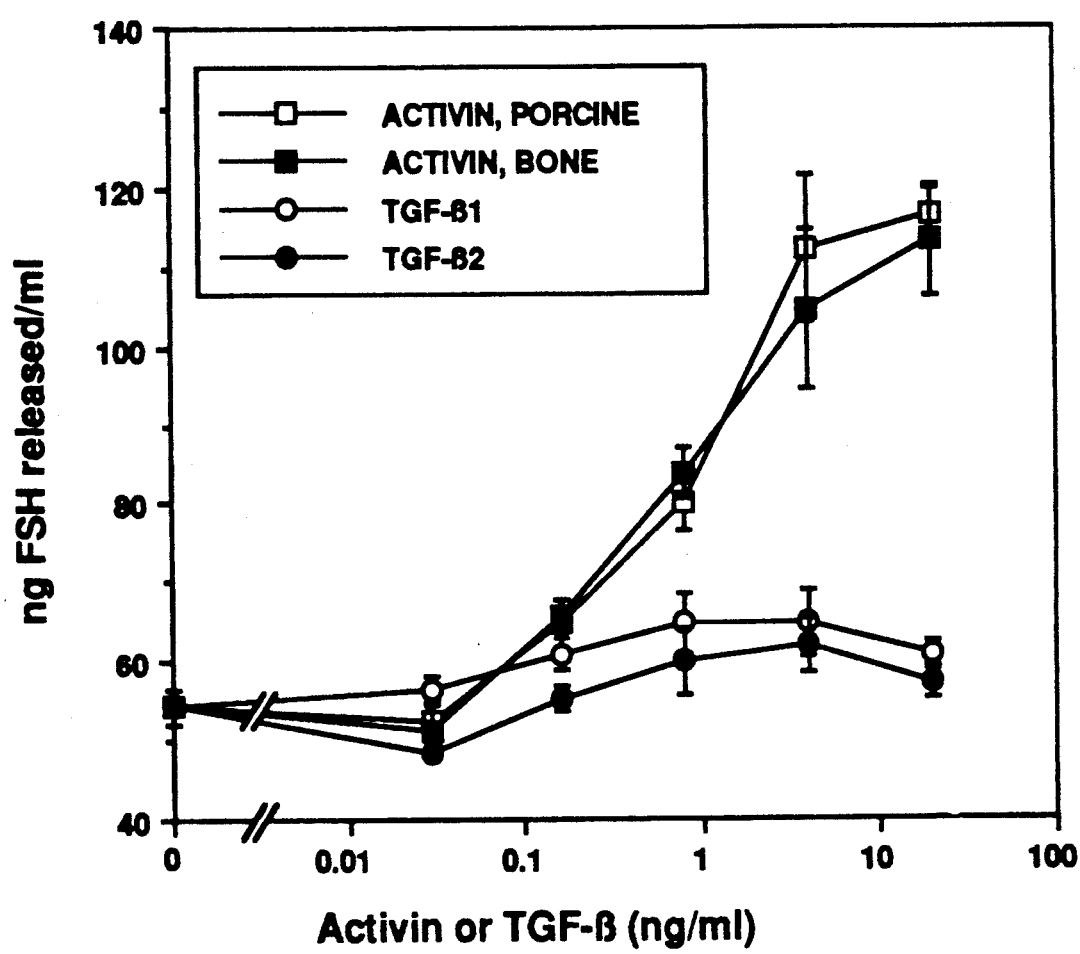
FIG. 1 is a graph of dose response curves regarding the release of FSH as described in Example 2.

It must be noted that as used in this specification and the appended claims, the singular forms "a", "an" and "the" include plural referents unless the context clearly dictates otherwise. Thus, for example, reference to "an activin" includes statistical mixtures of dimeric proteins of the type generally described herein; reference to "a bone morphogenetic protein" includes statistical mixtures of such proteins of the type described herein; and reference to "the method of administration" includes one or more methods of the type described herein and/or of the type which will become apparent to those of ordinary skill in the art upon reading this disclosure.

In general, the invention involves a method of inducing the deposition of mature bone tissue by administering an osteogenically effective amount of activin to a vertebrate subject in need of increased bone. The activin may be administered by itself or in combination with an additional growth factor such as TGF-$\beta$, BMP, or with bone marrow and/or proteins extracted therefrom. In accordance with one method of use, activin is administered (in combination with other growth factors and/or bone marrow) locally to the specific area in need of bone growth. Another method of treatment is carried out by administering an activin formulation systemically, thereby systemically inducing bone growth. In preferred embodiments, for local administration, activin in combination with BMPs and/or bone marrow, or proteins extracted therefrom, is administered in pharmaceutically acceptable excipients. For systemic administration, activin alone, or in combination with BMPs and/or bone marrow, or proteins extracted therefrom, is administered in pharmaceutically acceptable excipients.

Bone growth and maturation may be regulated by first administering an effective amount of TGF-$\beta$ and BMPs in pharmaceutically acceptable excipients, to induce massive bone growth, and secondly administering an osteogenically effective amount of activin, in pharmaceutically acceptable excipients, to induce bone maturation. Alternatively, bone growth and maturation may be regulated by administering effective amounts of TGF-$\beta$, BMPs, and activin, in pharmaceutically acceptable excipients.

The activin alone or in combination with other growth factors may be administered on a daily basis for 1–14 days, and more preferably 3–10 days, and most preferably about 7 days. The amount of activin alone or in combination with other growth factors which is administered will vary depending upon the size and particular needs of the patient. Therefore, the amount administered and the frequency and length of administration will be determined by the care giver depending on the needs and the patient responsiveness with respect to the particular formulation being administered. In general, the ratio of BMP to activin will be about 1:0.01 to about 1:100 by weight. When activin is used in combination with bone marrow, the ratio of activin to bone marrow will be about 0.001 $\mu$g:1 g to about 100 mg:1 g by weight.

B. Definitions

The term "activin" as used herein refers to activin $\beta$AA, activin $\beta$AB, activin $\beta$BB, and fragments thereof, synthetic peptides, and proteins having similar activity in a standard cell culture assay where the protein stimulates the release of follicular stimulating hormone (FSH) from rat pituitary cells (Vale, et al., *Nature* (1986) 321:776). Briefly, in this assay, anterior pituitaries from adult male Sprague-Dawley rats (200–220 g) are dissociated by collagenase and plated at a concentration of $0.33 \times 10^6$ cells per well in 24 well tissue culture dishes. The cells are allowed to recover for 72 hr in medium containing 2% fetal bovine serum (FBS). Following the recovery period, the cells are washed twice in fresh medium containing 2% FBS. All treatments are added at this time and the cells are incubated for 72 hr. The media is then collected and the FSH levels are determined using a radioimmunoassay kit provided by the National Hormone and Pituitary program of NIADDK.

For purposes of bone induction, activin may be isolated from natural sources or prepared by recombinant methods (R. H. Schwall et al., *Mol. Endo.* (1988) 2:1237–42). The primary sequence of activin is highly conserved from species to species (the activin $\beta$A chain is identical in human, porcine, bovine, and rat: Vale et al., *Recent Progress in Hormone Research* (1988) 44:1–34), as is the case with the TGF-$\beta$s. Thus, for example, it is expected that activin obtained from any vertebrate source will be useful in any vertebrate subject.

The term "BMPs" refers to a bone morphogenetic protein, or proteins isolated from bone, and fragments thereof and synthetic peptides which are capable of inducing bone deposition alone or when combined with appropriate cofactors such as TGF-$\beta$ (or activin). Preparation of BMPs is described in PCT/US87/01537, publication number WO 88/00205, which is incorporated herein by reference to disclose BMPs -1, -2, -3, and -4, and/or their method of administration. J. M. Wozney, in *Growth Factor Research*, Vol. 1 (1989), pp 267–280 describes three additional BMP proteins closely related to BMP-2, and which have been designated BMP-5, -6, and -7. WO 89/09787 and 89/09788 describe a protein called "OP-1," now known to be BMP-7. The cloning of BMP-7 is described in E. Ozkaynak et al., *EMBO Journal* (1990) 9:2985–2093, and the purification of BMP-7 is described in T. K. Sampath et al., *J. Biol. Chem.* (1990) 265:13198–13205.

The BMPs may also include proteins that induce elevated levels of bone formation when combined with appropriate growth factors such as TGF-$\beta$ or activin.

The term "TGF-$\beta$" refers to beta-type transforming growth factors, including TGF-$\beta$1, TGF-$\beta$2, TGF-$\beta$3, TGF-$\beta$4, TGF-$\beta$5, heterodimers of the TGF-$\beta$ polypeptide chains (e.g. TGF-$\beta$1.2), and fragments thereof, synthetic peptides, and homologous proteins (having substantially equivalent biological activity in the TGF-$\beta$ assay described in *Methods for Preparation of Media, Supplements, and Substrate for Serum-free Animal Cell Culture* (1984) pp. 181–194. Alan R. Liss, Inc.).

The assay determines ability to induce anchorage-dependent growth in non-neoplastic normal rat kidney (NRK) fibroblasts by measuring the formation of cell colonies in soft agar. Preparation of TGF-$\beta$1 and TGF-$\beta$2 is described in U.S. Pat. No. 4,774,322, incorporated herein by reference. Additional TGF-$\beta$s have also been described. U.S. Pat. No. 4,886,747 describes the identification of TGF-$\beta$3 and its nucleotide sequence, and describes a method for recovery of TGF-$\beta$ from recombinant cell cultures. S. B. Jakowlew et al., *Molec. Endocrinol.* (1988) 2:1186–1195, describes TGF-$\beta$4 and its nucleotide sequence, identified by cDNA characterization. A. B. Roberts et al., *Growth Factors*, Vol. 2 (1990) pp. 135–147, describes the purification of TGF-$\beta$5 from *Xenopus*-conditioned medium.

The term "bone growth" relates to bone mass. TGF-$\beta$ is thought to increase bone mass systemically. This is suggested by the increase in the number and size of osteoblasts, and increased deposition of osteoid lining bone surfaces following systemic administration.

The term "mature bone" relates to bone that is mineralized, in contrast to non-mineralized bone such as osteoid. Administration of activin results in a stimulation of mature, mineralized bone formation whereas TGF-$\beta$ preferentially stimulates formation of new osteoid.

The term "osteogenically effective" means that amount which effects the formation and development of mature bone.

The term "subject" as used herein refers to a living vertebrate animal such as a mammal or bird in need of treatment, i.e., in need of bone induction. Such need arises in cases of bone fracture, nonunion, defect, prosthesis implantation, and the like. Such need also arises in cases of systemic bone disease, as in osteoporosis.

The term "treatment" as used herein shall mean (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

C. General Methods

BMPs and TGF-$\beta$s are prepared by methods known in the art (see e.g., PCT/US87/01537 and U.S. Pat. No. 4,774,322 which are incorporated herein by reference to disclose such), or are available from commercial sources (R&D Systems, Minneapolis, Minn.). Activin may be isolated from follicular fluid, prepared by recombinant methods, or isolated from bone using the methods disclosed below.

Activin is similar in hydrophobicity to TGF-$\beta$1 and TGF-$\beta$2 (but has a lower pI than these polypeptide factors) and is isolated from bone in a similar fashion. J. M. Vaughan et al., *Meth. Enzymol.* (1989) 168:588–617, describes a method for preparing anti-activin $\beta$A antibody. It is well known in the art that antibodies are useful in isolation and purification procedures. Alternatively, a detailed isolation procedure in accordance with the present invention is described in Example 1 below. The characterization of activin is described in Example 2 below.

Pharmaceutical formulations of the invention which include activin for administration will generally include an osteogenically effective amount of activin, and optionally, BMP, to promote bone growth, in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. A presently preferred vehicle comprises about 1 mg/ml serum albumin (species-specific) in phosphate-buffered saline (PBS). A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

Compositions of the invention may also be implanted directly at the site to be treated, for example, by injection or surgical implantation of the composition in a sustained-release carrier. Suitable carriers include hydrogels, controlled- or sustained-release devices (e.g., an Alzet ® minipump), polylactic acid, and collagen matrices. Presently preferred carriers are formulations of atelopeptide collagen containing particulate calcium phosphate mineral components, such as combinations of fibrillar atelopeptide collagen (for example Zyderm ® Collagen Implant, available from Collagen Corporation, Palo Alto, Calif.) with hydroxyapatite-tricalcium phosphate (HA-TCP, available from Zimmer, Inc., Warsaw, Ind.). It is presently preferred to administer implant compositions containing activin and BMP in a collagen/mineral mixture implant.

The proteins of the invention may be conjugated to other molecules to increase their water-solubility, increase their half-lives, or enhance their ability to bind to bone. For instance, they may be conjugated to polyethylene glycol to increase their water solubility or to bone-binding molecules such as bisphosphonates (e.g. 1-hydroxyethylidene-1,1-bisphosphonic acid, dichloromethylene bisphosphonic acid, and 3-amino-1-hydroxypropylidene-1-bisphosphonic acid) and fluorochromes (e.g. tetracyclines, calcein blue, xylenol orange, calcein green, and alizarin complexone red) to target the proteins to bony sites. Various agents for conjugating molecules to proteins are well known in the art and include aldehydes, carbodiimides, and other bifunctional moieties.

The precise dosage necessary will vary with the age, size, sex and condition of the subject, the nature and severity of the disorder to be treated, and the like; thus, a precise effective amount cannot be specified in advance and will be determined by the care giver. However, appropriate amounts may be determined by routine experimentation with animal models, as described below. In general terms, an effective dose of activin for systemic treatment will range from about 0.001 $\mu$g/kg to about 10 mg/kg of body weight. An effective dose for BMP is about 0.001 $\mu$g/kg to about 10 mg/kg of body weight.

An effective dose for activin for local treatment will range from about 0.001 $\mu$g/kg to about 10 mg/kg of body weight. An effective dose of BMP for local treatment is substantially the same as the dose of activin.

In addition, it may be desirable to combine the proteins with other therapeutics, such as, for instance in the case of osteoporosis, fluoride, calcitonin, vitamin D metabolites, estrogen, and parathyroid hormone. Because proteins are non-species-specific in their activity they maybe used to treat subjects in general, including sport, pet, and farm animals, and humans.

Suitable animal models for bone growth and maturation include the mouse model as illustrated in Examples 3, 4 and 5 below. Briefly, systemic treatment is assayed by injecting test amounts of activin into a mouse or other experimental animal following a standard protocol, followed by examination of bone strength and mass at approximately 14 days post-administration. Such examination may be performed in situ by using imaging techniques (e.g., nuclear magnetic resonance imaging, X-ray tomography, ultrasound, and sound conduction) or stress testing, or ex vivo by standard histological methods. Suitable dosages and protocols will result in improved deposition of mature bone, for example, increased cortical thickness in long bones.

Compositions of the invention are useful for treating bone fractures, defects, and disorders which result in weakened bones such as osteoporosis, osteohalisteresis, osteomalacia, and age-related loss of bone mass. Compositions of the invention that are delivered in sustained-release vehicles are also particularly useful for improving implant fixation, for example for improving ingrowth of new bone into a metal prosthesis in joint reconstruction and dental or orthopedic implants.

Dental and orthopedic implants can be coated with osteoinductive proteins, such as BMP, activin, TGF-$\beta$, and bone marrow or proteins extracted therefrom, either in combination or alone, to enhance attachment of the implant device to the bone. Implant devices generally have a porous end, which is inserted into the implant site. The porous end allows the new bone to grow into the porous space and hold the implant in place. The greater the growth of new bone into the porous space, more solidly the implant is held in place. The presence of osteoinductive proteins, such as BMP, activin, and TGF-$\beta$, and bone marrow or proteins extracted therefrom, either alone or in combination, in the porous space is expected to enhance the growth of new bone into the porous space.

In general, implant devices may be coated with osteoinductive proteins as follows. Activin, BMP, and TGF-$\beta$, and bone marrow or proteins extracted therefrom, either alone or in combination, are dissolved at a concentration in the range of 0.01 $\mu$g/ml to 200 mg/ml in phosphate-buffered saline (PBS) containing 2 mg/ml serum albumin. The porous end of an implant is dipped in the solution and is airdried or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the osteoinductive factor is mixed with collagen gel (e.g. Zyderm® Collagen Implant, Collagen Corp., Palo Alto, Calif.) to a final collagen concentration of 5 mg/ml to 100 mg/ml to form a paste, which is then used to coat the porous end of the implant device. The coated implant device is placed into the bony site immediately or is airdried and rehydrated with PBS prior to implanting.

Either native or synthetic (recombinant) activin can be used to produce antibodies, both polyclonal and monoclonal. The term "antibody" is intended to include whole immunoglobulin of any isotype or species as well as antigen binding fragments and chimeric constructs. If polyclonal antibodies are desired, purified activin is used to immunize a selected mammal (e.g. mouse, rabbit, goat, horse, etc.) and serum from the immunized animal later collected and treated according to known procedures. Compositions containing polyclonal antibodies to a variety of antigens in addition to activin can be made substantially free of antibodies which are not anti-activin antibodies by passing the composition through a column to which activin has been bound. After washing, polyclonal antibodies are eluted from the column. Monoclonal anti-activin antibodies can also be readily produced by one skilled in the art. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus, M. Schrier *Hybridoma techniques* (1980); Hammerling et al., *Monoclonal Antibodies and T cell Hybridomas* (1981); Kennett et al., *Monoclonal Antibodies* (1980).

By employing activin (native or synthetic) as an antigen in the immunization of the source of the B cells immortalized for the production of monoclonal antibodies, a panel of monoclonal antibodies recognizing epitopes at different sites on the activin molecule can be obtained. Antibodies which recognize an epitope in the binding region of the protein can be readily identified in competition assays between antibodies and proteins. Antibodies which recognize a site on the activin protein are useful, for example, in the purification of the protein from cell lysates or fermentation media, in the characterization of the protein, and in identifying immunologically related proteins. Such immunologically related proteins (i.e. that exhibit common epitopes with activin) are another aspect of the invention. In general, as it is known in the art, the anti-activin antibody is fixed (immobilized) to a solid support, such as a column or latex beads, contacted with a solution containing activin, and separated from the solution. The activin, bound to the immobilized antibodies, is then eluted.

Methods for inducing local bone growth and maturation comprise administering an osteogenically effective amount of activin, in combination with BMPs, bone marrow, or proteins extracted therefrom, in a pharmaceutically acceptable carrier, as describe in Example 3, below.

Methods for inducing systemic bone growth and maturation comprises administering an osteogenically effective amount of activin alone, and optionally including BMPs, bone arrow, or proteins extracted therefrom, in a pharmaceutically acceptable carrier, as described in Example 4, below.

Methods for regulating bone growth and maturation comprises initially administering an effective amount of TGF-$\beta$ and BMPs, and sequentially administering an effective amount of activin. Preferably, to induce endochondral bone growth, combinations of BMP and TGF-$\beta$ may be locally administered to induce cartilage modeling. Activin may be subsequently administered subcutaneously and/or systemically to induce mature bone formation and differentiation of the cartilage model induced by TGF-$\beta$ and BMP. The activin would enhance mineralization of the endochondral bone and maturation. It is expected that the quantity of mature bone formed by this method would be greater than the quantity of mature bone formed by either (i) TGF-$\beta$, BMPs, or activin alone, or (ii) combinations of TGF-$\beta$ and BMPs, or (iii) combinations of activin and BMPs.

Alternative methods for regulating bone growth and maturation comprise (i) locally administering an osteogenically effective amount of activin with TGF-$\beta$, BMP and/or bone marrow or proteins extracted therefrom, to induce bone growth and maturation, or (ii) systemically administering effective amounts of TGF-$\beta$, BMP and/or bone marrow or proteins extracted therefrom to induce bone growth, followed by systemically administering an osteogenically effective amount of activin to induce bone maturation.

Activin is extracted from demineralized bone powder with 6M guanidine HCl, 10 mM EDTA, pH 6.8. The extract is fractionated by gel filtration chromatography. The pool of fractions containing TGF-$\beta$ is desalted and fractionated by cation exchange chromatography. The pool of fractions containing activin is then fractionated by C18 RP-HPLC, using a linear acetonitrile gradient in 0.1% trifluoroacetic acid (TFA). Activin elutes between TGF-$\beta$1 and TGF-$\beta$2. The activin fraction is applied onto a cation exchange Mono-S FPLC column (Pharmacia) at pH 4.6. The column is equilibrated sequentially into pH 6.7 and pH 9.0 buffers. Activin, which elutes during the pH 6.7–9.0 gradient, is desalted by C18 RP-HPLC performed in 0.1% TFA with a linear acetonitrile gradient as the final purification step.

Since TGF-$\beta$1 and TGF-$\beta$2 have similar chromatographic properties as activin, activin preparations may be contaminated with low levels of TGF-$\beta$. The majority of the contaminating TGF-$\beta$ activity may be removed during the pH 4.6–6.7 gradient performed on the Mono-S FPLC, resulting in substantially pure preparations of activin. In addition, the majority of TGF-$\beta$2 elutes slightly later than activin during the pH 6.7–9.0 gradient, while TGF-$\beta$1 is retained on the column during the Mono-S FLPC step. The use of a two step salt gradient, as compared to standard techniques using a single step salt gradient, is a unique chromatographic procedure which results in significantly pure preparations of activin.

D. Examples

The following examples are put forth so as to provide those of ordinary skill in the art with a complete disclosure and description of how to extract, isolate, formulate and use the compositions and methods of the invention and are not intended to limit the scope of what the inventors regard as their invention. Efforts have been made to insure accuracy with respect to numbers used (e.g., amounts, times, temperature, etc.), but some experimental error and deviations should be accounted for. Unless indicated otherwise, parts are parts by weight, temperature is in degrees centigrade, pressure is at or near atmospheric, and other parameters are conventional and in accordance with those normally accepted by those skilled in the art.

EXAMPLE 1

Extraction and Isolation of Activin

Activin $\beta$AA was isolated and purified from 75 kg of bovine bone powder using the procedure described below. The extract of demineralized bone powder was prepared from fresh metatarsal and metacarpal bones as described by Seyedin et al., U.S. Pat. No. 4,774,322.

Crude bone extract in 6M guanidine HCl, 10 mM EDTA, pH 6.8, was fractionated by column chromatography on Sephacryl ® S-200, and the fractions containing high levels of TGF-$\beta$ were pooled. The TGF-$\beta$ pool was concentrated by ultrafiltration and was desalted by passage through an Amicon GH-25 column equilibrated in 6M urea, 50 mM sodium acetate, 10 mM NaCl, pH 4.6.

The NaCl concentration of the TGF-$\beta$ pool was increased to 70 mM, and the product applied onto a Whatman ® CM-52 column (2.5×38 cm) equilibrated in a buffer of 6M urea, 50 mM sodium acetate, 70 mM NaCl, 1% isopropanol, pH 4.6. The urea/acetate buffer was pumped through the column until $A_{280}$ returned to the baseline. The bound protein was eluted using a linear 70–600 mM NaCl gradient (1000 ml total volume) in the urea/acetate buffer at a flow rate of 30 ml/hour. The CM-52 fractions were analyzed by SDS-PAGE (U. Laemmli, *Nature* (1970) 227:680–85) on a 15% polyacrylamide gel, and three separate CM-bound pools were made. Pools 2 (fractions 61–70) and 3 (fractions 71–83) contained the majority of TGF-$\beta$2 and TGF-$\beta$1, respectively. Pool 1, which consisted of fractions 55–60, contained the majority of activin.

Each of the pools was individually chromatographed on a C18 RP-HPLC column (1×25 cm, Vydac, 218TP510) equilibrated in 0.1% trifluoroacetic acid (TFA). The bound protein was eluted from the column using a linear gradient of acetonitrile from 32–52% buffer B (90% acetonitrile, 0.1% TFA) over 20 minutes at a flow rate of 3 ml/minute. Fractions were collected manually in order to isolate individual peaks, and the fractions were analyzed by SDS-PAGE under nonreducing conditions. A 25 kD protein (activin) migrating slightly faster than TGF-$\beta$ on an SDS-polyacrylamide gel was observed to elute from the reverse-phase HPLC column between the elution positions of TGF-$\beta$1 and TGF-$\beta$2 in the CM-bound pools 1 and 2. The CM-bound pool 3, which contained the majority of the TGF-$\beta$1, was later shown to contain very little activin, and no further attempts were made to isolate it from pool 3.

The 25 kD protein (activin) fractions from the CM-bound pools 1 and 2 were combined. The pool was diluted 3-fold with 6M urea, 50 mM sodium acetate, 10 mM NaCl, 1% isopropanol, pH 4.6, and was loaded onto a Mono-S FPLC column (Pharmacia HR5/5), which was equilibrated in the same buffer. Some of the bound proteins eluted when the pH was raised from 4.5 to 6.7 by equilibrating the column into 6M urea, 50 mM sodium acetate, 10 mM NaCl, 1% isopropanol, pH 6.7 at a flow rate of 0.5 ml/min over a 10 minute period. The column was then equilibrated into 6M urea, 20 mM HEPES, 10 mM NaCl, 1% isopropanol, pH 6.7, and the 25 kD protein (activin) was eluted by equilibrating the column into 6 mM urea, 20 mM HEPES, 10 mM NaCl, 1% isopropanol, pH 9.0, at a flow rate of 0.5 ml/min over a 10 min period.

A linear NaCl gradient from 10–400 mM NaCl in urea/HEPES buffer, pH 9.0, at a flow rate of 0.5 ml/min over a 10 min period, was then used to elute remaining bound proteins. The SDS-polyacrylamide gels were stained with silver (J. H. Morrisey, *Anal. Biochem.* (1981) 117:301–310). The majority of TGF-$\beta$ activity, which would otherwise contaminate activin, was removed by performing the pH 4.7–6.7 gradient. Activin eluted during the pH 6.7–9.0 gradient. The elution position of activin is slightly before that of TGF-$\beta$2 during the pH 6.7–9.0 gradient. TGF-$\beta$1 elutes during the 10–400 mM NaCl gradient at pH 9.0.

Some 25 kD TGF-$\beta$-like protein (including TGF-$\beta$1) eluted during the NaCl gradient and was highly contaminated with low molecular weight proteins (12 kD to 18 kD).

The 25 kD protein (activin) was chromatographed on a C18 RP-HPLC column as the final purification step. The pool of 25 kD protein fractions from the pH 6.7–9.0 gradient of the Mono-S chromatography was acidified by adding glacial acetic acid to a final concentration of 1.0M, and was applied to a C18 RP-HPLC analytical column (Vydac, 4.6×250 mm, 218TP54) equilibrated in 0.1% TFA. The column was run at a flow rate of 1 ml/min, and the bound protein was eluted using a linear acetonitrile gradient from 32-52% buffer B at a rate of 1% buffer B/min. Fractions were analyzed by SDS-PAGE under nonreduced conditions. The activin fraction demonstrated one single major band on the silver-stained SDS-polyacrylamide gel. No other bands were seen. The total yield of the 25 kD protein (activin) from the CM-bound pools 1 and 2 was approximately 1.2 mg, corresponding to 16 $\mu$g/kg bone powder.

EXAMPLE 2

Identification of the 25 kD Protein as Activin

A) The N-terminus of the 25 kD protein obtained in Example 1 above was sequenced on an Applied Biosystems sequencer. The first 36 amino acids were Gly-Leu-Glu-(?)-Asp-Gly-Lys-Val-Asn-Ile-(?)-(?)-Lys-Lys-Gln-Phe-Phe-Val-Ser-Phe-Lys-Asp-Ile-Glu-Trp-Asn-Asp-Trp-Ile-Ile-Ala-Pro-Ser-Gly-Tyr-His (where "?" denotes an unidentified amino acid). This sequence corresponds to the first 36 amino acid residues at the N-terminus of the activin $\beta$A subunit, in which each of the "?"s is Cys (Cys is not detected in the sequencing process). No other amino acid sequences were observed. The entire activin $\beta$A subunit sequence, in single letter code, is

```
GLECDGKVNICCKKQFFVSF
KDIGWNDWIIAPSGYHANYC
EGECPSHIAGTSGSSLSFHS
TVINHYRMRGHSPFANLKSC
CVPTKLRPMSMLYYDDGQNI
IKKDIQNMIVEECGCS
```

(W. Vale et al., *Recent Progress in Hormone Research* (1988) 44:1–34.

(B) A 5 $\mu$g sample of the activin obtained in Example 1 above was reduced and denatured by incubating for 2 hours at 50° C. under N$_2$ atmosphere in 250 $\mu$L of alkylation buffer (0.4M Tris/HCl, pH 8.5, 6M urea, 0.1% EDTA, 20 mM DTT). The reduced protein was alkylated by incubating in the presence of 100 mM iodoacetamide at room temperature in the dark for 4 hrs. The sample was subjected to SDS-PAGE.

The silver-stained gel of reduced and alkylated 25 kD protein exhibited a single band migrating at a molecular weight of 14 kD. This observation is consistent with the 25 kD protein being activin, where activin is known to be a dimer of two 14 kD subunits.

(C) The activin extracted and isolated in Example 1 above was assayed for biological activity by testing the ability to stimulate release of follicle-stimulating hormone (FSH) by rat pituitary cells in culture following the method of W. Vale et al., *Endocrinology* (1972) 91:562–572. Briefly, anterior pituitaries from adult male Sprague-Dawley rats (200–220 g) were dissociated by collagenase and plated at a concentration of 0.33-10$^6$ cells per well in 24-well tissue culture dishes. The cells were allowed to recover for 72 hours in medium containing 2% fetal bovine serum (FBS). Following the recovery period, the cells were washed twice in medium containing 2% FBS. All treatments were added at this time and the cells were incubated for 72 hr. The media was then collected and FSH levels determined using a radioimmunoassay kit provided by the National Hormone and Pituitary Program of NIADDK. The protein isolated in Example 1 exhibited FSH-releasing activity equal to activin derived from porcine follicular fluid. TGF-$\beta$1 and TGF-$\beta$2 did not exhibit FSH-releasing activity, as expected. The results are shown in FIG. 1. The results described in (A), (B) and (C) demonstrate that the 25 kD protein purified from bone in Example 1 is activin $\beta$A homodimer.

The activin purified from bovine bone, as described in Example I, was assayed for the protein's ability to stimulate formation of erythroid colonies following the method of Broxmeyer et al., *Proc. Natl. Acad. Sci. U.S.A.* (1988) 85:9052–6. Single cell suspensions of normal C57B1/6 male murine femur bone marrow and spleen were prepared for in vitro assay. Activin stimulated increases in the colony-forming unit erythroids (CFU-E) and burst-forming unit erythroid (BFU-E) in a dose-dependent fashion in the similar range of activin concentration as those reported for recombinant human activin (Broxmeyer et al., *Proc. Natl. Acad. Sci. U.S.A.* (1988) 85:9052–6). Activin also significantly stimulated both the CFU-E and BFU-E of spleen cells. The results are summarized in Table I below.

TABLE ONE

Effects of activin on erythroid colony formation

Bone marrow (BM)

| GROUP | CFU-E/ 10 5 BM | % CONTROL | BFU-E/ 10 5 BM | % CONTROL |
|---|---|---|---|---|
| Control | 215 ± 38 | 100 | 10 ± 2 | 100 |
| Activin 100 ng/ml | 309 ± 32** | 143 | 19 ± 1** | 188 |
| 50 ng/ml | 296 ± 15 | 138 | 16 ± 2* | 163 |
| 25 ng/ml | 269 ± 25 | 125 | 16 ± 4* | 155 |
| 12.5 ng/ml | 245 ± 51 | 114 | 15 ± 4 | 150 |
| 6.25 ng/ml | 239 ± 22 | 111 | 13 ± 3 | 125 |
| 3.12 ng/ml | 229 ± 20 | 106 | 10 ± 2 | 100 |
| 1.56 ng/ml | 215 ± 34 | 100 | 10 ± 2 | 100 |

| Spleen | BFU-E/10$^5$ | % control | CFU-E/10$^5$ | % control |
|---|---|---|---|---|
| control | 2.4 + 0.4 | 100 | 255 + 16 | 100 |
| 50 ng/ml activin | 7 + 1 | 271 | 429 + 20 | 168 |

EXAMPLE 3

Local Induction of Bone Growth and Maturation

The following experiment demonstrated induction of bone growth in vivo using a combination of BMP and activin.

A ceramic/collagen carrier was prepared using hydroxyapatite, tricalcium phosphate, and soluble bovine dermal collagen (VITROGEN ® collagen-in-solution, Collagen Corporation) as described by H. Bentz et al., *J. Biol. Chem.* (1989) 264:20805–810. BMP was prepared as described in E. A. Wang et al., *Proc. Natl. Acad. Sci. USA* (1988) 85:9484–88. Activin was obtained as described in Example 1 above.

Compositions were prepared as follows:

A: Carrier alone
1: BMP (1 $\mu$g)
2: BMP (1 $\mu$g), TGF-$\beta$2 (7.5 $\mu$g)
3: BMP (1 $\mu$g), TGF-$\beta$2 (2.5 $\mu$g)

4: BMP (1 μg), activin (7.5 μg)
5: BMP (1 μg), activin (2.5 μg)
6: BMP (1 μg)+TGF-β2 (7.5 μg) +activin (7.5 μg).
7: activin (2.5 μg)

The compositions were then implanted at the ectopic subcutaneous sites in the ventral thorax region of male Sprague-Dawley rats at 6 rats/composition (except for carrier alone, BMP alone, and activin alone, at 4 rats/composition. After 14 days, the implants were excised, evaluated biochemically for alkaline phosphatase activity (Bentz et al., *J. Biol. Chem.* (1989) 264:20805–20810; Reddi et al., *Proc. Natl. Acad. Sci. U.S.A.* (1972) 69:1601–5) and examined histologically for bone growth. The biochemical results are shown graphically in FIG. 2.

Biochemistry

Implants containing BMP or activin alone exhibited very low alkaline phosphatase activity. (See columns 1 and 7 in FIG. 2.) The compositions containing BMP and either TGF-β2 or activin or both (at either dosage) exhibited high levels of alkaline phosphatase activity.

Histology:

Compositions containing carrier alone, or carrier with activin, exhibited no bone growth, and displayed mild to moderate foreign body reactions. Compositions containing BMP alone exhibited low to moderate levels of bone and no cartilage.

Compositions containing BMP and TGF-β2 exhibited a large increase in both bone and cartilage. Composition 3 (2.5 μg TGF-β2) exhibited more bone, and more differentiation of the bone tissue, than composition 2 (7.5 μg TGF-β2). Composition 2 induced more cartilage than bone.

Compositions containing BMP and activin (4 and 5) exhibited little or no cartilage, and significantly elevated levels of deposited mature bone. Composition 5 (2.5 μg activin) induced deposition of more bone than composition 6 (7.5 μg activin). However, both compositions induced very little cartilage deposition, and produced more mature bone than that obtained using BMP with TGF-β2.

Composition 6 (BMP, TGF-β2, and activin) induced a poorly differentiated, disorganized mixture of bone, fibrocartilage, and fibrosis.

The experimental results demonstrated that activin functions as an osteogenic cofactor for BMP in vivo, and induces growth of high-quality mature bone, without inducing cartilage formation.

EXAMPLE 4

Systemic Administration of Activin

The following experiment demonstrated the activity of activin upon systemic administration in vivo.

Neonatal Mice

Neonatal mice (Swiss-Webster, 8–10 litters per group) were given daily administrations of:
1: 1 μg TGF-β1
2: 1 μg activin
3: 3 μg activin
4: 1 μg TGF-β1+1 μg activin
5: vehicle alone in a vehicle of 37.5 μg mouse serum albumin (MSA) in 25 μl PBS. The control group received vehicle alone. The compositions were administered daily for 4 days, by subcutaneous injection in the nape of the neck. The femurs were harvested on the fifth day, and examined histologically.

The mice receiving 1 μg/day activin exhibited superior bone growth and maturation, displaying reduced porosity in the femoral shaft compared with controls. In contrast, mice receiving 1 μg/day TGF-β1 exhibited increased porosity compared with controls. Both groups exhibited increased levels of osteoclasts, and hypertrophy of osteoblasts relative to controls, suggesting increased bone remodeling. However, the group receiving 3 μg/day activin exhibited decreased levels of osteoclasts, and flat, inactive-appearing osteoblasts. Administration of activin and TGF-β1 together inhibited the changes in osteoclasts and osteoblasts, and did not increase femoral shaft porosity. The results are graphically shown in FIG. 3.

The results indicate that systemic administration of activin for a limited treatment course improves bone growth and maturation by inducing bone formation and promoting bone remodeling.

EXAMPLE 5

Activin Enhances Osteogenesis in Bone Marrow

Implantation of bone marrow in collagen/hydroxyapatite-tricalcium phosphate ceramic carrier in rat subcutis results in local bone formation in the ceramic implant at ectopic sites. This process, known as osteogenesis, is probably due to differentiation of a specific cell population in the bone marrow. Activin, when added to the bone marrow, promotes greater mature bone deposition.

Young adult male Lewis rats (8 weeks old, 3 rats/group) were implanted subcutaneously in the ventral thorax region with ceramic carrier containing 25 or 50 μl of rat bone marrow plus 5 μg of activin or TGF-β2. After 14 days, the implants were excised, evaluated for alkaline phosphatase activity and examined histologically for bone formation.

Figure 4:
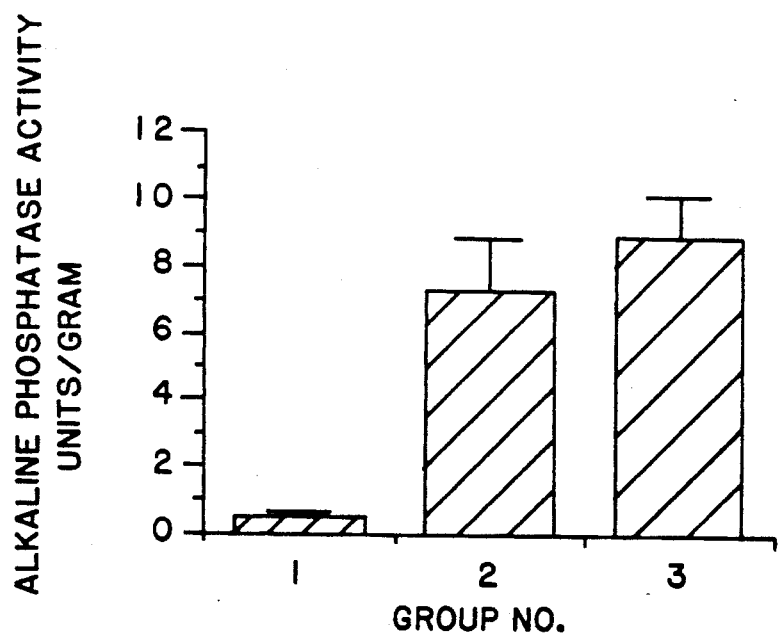
FIG. 4 is a graph of the results obtained in an alkaline phosphatase assay at 14 days, as described in Example 5.

Ceramic carrier alone had almost no alkaline phosphatase activity and histologically, exhibited low levels of inflammatory cells and no bone. Ceramic carrier with 20 μl of bone marrow exhibited low levels of bone formation. However, the group with 20 μl of bone marrow plus activin showed elevated levels of bone formation over the levels observed with 20 μl of bone in the implants of bone marrow alone and bone marrow plus activin when compared with the carrier alone (FIG. 4). In a second study, 10 μl of bone marrow plus TGF-β2 showed less bone and a higher level of fibrosis than the group with bone marrow plus activin. Although the alkaline phosphatase activity was elevated, it was less than the level observed with bone marrow plus activin. These experimental results demonstrate that activin uniquely enhances bone formation with the absence of fibrosis when administered with bone marrow.

The present invention is shown and described herein and was considered to be the most practical, and preferred embodiment. It is recognized, however, that departures may be made therefrom which are within the scope of the invention and that obvious modifications will occur to one skilled in the art upon reading this disclosure.

We claim:

1. A method for inducing deposition and maturation of bone in a subject in need thereof, which comprises administering an osteogenically effective amount of activin in a pharmaceutically acceptable excipient to said subject.

2. The method of claim 1, wherein the activin in a pharmaceutically acceptable excipient is administered systemically to the subject.

3. The method of claim 1, wherein the activin is administered once per day for about 1-14 days.

4. The method of claim 1, wherein said subject has osteoporosis.

5. The method of claim 1, wherein the pharmaceutically acceptable excipient comprises a mixture of collagen and calcium phosphate.

6. The method of claim 1, which further comprises administering an effective amount of TGF-$\beta$ to the subject.

7. The method of claim 6, wherein said activin and the TGF-$\beta$ are administered simultaneously.

8. The method of claim 6, wherein said activin and said TGF-$\beta$ are administered sequentially.

9. The method of claim 1, which further comprises administering an effective amount of a BMP to the subject.

10. The method of claim 9, wherein said activin and said BMPs are administered in a ratio of about 1:0.01 to about 1:100 by weight.

11. The method of claim 9, wherein said activin and said BMPs are administered in a ratio of about 1:0.1 to about 1:1 by weight.

12. The method of claim 9, wherein said activin and said BMP administered systemically to the subject.

13. The method of claim 9, wherein said activin and said BMP are administered once per day for about 1-14 days.

14. The method of claim 9, wherein said subject has osteoporosis.

15. The method of claim 9, wherein said activin and said BMP are administered simultaneously.

16. The method of claim 9, wherein said activin and said BMP are administered sequentially.

17. The method of claim 9, which further comprises administering an effective amount of TGF-$\beta$ to the subject.

18. The method of claim 1, which further comprises administering an effective amount of bone marrow to the subject.

19. The method of claim 18 wherein said activin and said bone marrow are administered once per day for about 1-14 days.

20. The method of claim 18 wherein said subject has osteoporosis.

21. The method of claim 18, which further comprises administering an effective amount of TGF-$\beta$ to the subject.

22. The method of claim 18, wherein said activin and said bone marrow are present in a ratio of about 0.001 $\mu$g:1 g to about 100 mg:1 g by weight.

23. The method of claim 18, wherein said bone marrow and said activin are administered in a composition comprising collagen and calcium phosphate.

24. The method of claim 18, wherein said activin and said bone marrow are administered simultaneously.

25. The method of claim 18, wherein said activin and said bone marrow are administered sequentially.

26. The method of claim 3 wherein the activin is administered once per day for about 3-10 days.

27. The method of claim 26 wherein the activin is administered once per day for about 7 days.

28. The method of claim 13 wherein said activin and said BMP are administered once per day for about 3-10 days.

29. The method of claim 28 wherein said activin and said BMP are administered once per day for about 7 days.

30. The method of claim 19, wherein said activin and said bone marrow are administered once per day for about 3-10 days.

31. The method of claim 30, wherein said activin and said bone marrow are administered once per day for about 7 days.

* * * * *